(12) United States Patent
Smith et al.

(10) Patent No.: US 7,767,414 B1
(45) Date of Patent: Aug. 3, 2010

(54) OPTICAL IMAGING OF MOLECULAR CHARACTERISTICS OF BIOLOGICAL SPECIMEN

(75) Inventors: Stephen J. Smith, Los Altos, CA (US); Kristina D. Micheva, San Jose, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 934 days.

(21) Appl. No.: 11/408,139

(22) Filed: Apr. 20, 2006

Related U.S. Application Data (60) Provisional application No. 60/673,590, filed on Apr. 20, 2005.

(51) Int. Cl.
*G01N 1/30* (2006.01)
(52) U.S. Cl. .................. 435/40.52; 435/1.1; 435/2; 435/7.2; 435/40.51; 435/395; 435/396; 435/397; 436/63; 436/64; 436/518
(58) Field of Classification Search .................. 435/1.1, 435/1.2, 2, 6, 7.1, 7.2, 40.5, 40.52, 395, 396, 435/397; 436/63, 64, 518
See application file for complete search history.

(56) References Cited

OTHER PUBLICATIONS

Kuzirian et al., Oxygen Plasma Etching of Entire Block Faces Improves The Resolution and Usefulness of Serial Scanning Electron Microscopic Images, Scanning Electron Microscopy 4: 1877-1885 (1983).*

Rosenthal et al., Rapid High Resolution Three Dimensional Reconstruction of Embryos with Episcopic Fluorescence Image Capture, Birth Defects Research, Part C, 72: 213-223 (2004).*

Sukhanova et al., Biocompatible fluorescent nanocyrstals for immunolabeling of membrane proteins in cells, Analytical Biochemistry 324: 60-67 (2004).*

Coulter et al., Video-Enhanced Technique for Detecting Neurophysin, Enkephalin, and Somatostatin Immunoreactivity in Ultrathin Sections of Cat Median Eminence, The Journal of Histochemistry and Cytochemistry 35 (11): 1405-1415 (1986).*

Ewald et al., Surface Imaging Microscopy, An Automated Method for Visualizing Whole Embryo Samples in Three Dimensions at High Resolution, Developmental Dynamics 225: 369-375 (2002).*

Wali et al., A method for collecting semithin epoxy serial sections for light microscopy and 3-D reconstruction, Journal of NeuroScience Methods 23: 91-94 (1988).*

Andew J. Ewald et al. "Surface Imaging Microscopy, An Automated Method for Visualizing Whole Embryo Samples in Three Dimensions at High Resolution." 2002 Wiley-Liss, Inc. *Developmental Dynamics*, vol. 225:369-375.

(Continued)

*Primary Examiner*—Gailene R Gabel
(74) *Attorney, Agent, or Firm*—Crawford Maunu PLLC (57) ABSTRACT

Imaging specimen such as biological tissue is facilitated. According to an example embodiment of the present invention, a relatively thin, surface portion of a specimen is stained and imaged. The thin portion is removed, exposing a new portion of the specimen. The newly-exposed portion is stained and imaged. Subsequent new surface portions (newly exposed) are similarly stained and imaged, with multiple images obtained from the specimen in an automated fashion. Some applications are directed to the distinct imaging of specimen characteristics having relatively small vertical separation (e.g., less than about 40 nanometers), with an upper characteristic imaged, removed, and the lower characteristic subsequently imaged.

26 Claims, 7 Drawing Sheets

OTHER PUBLICATIONS

Julie Rosenthal et al. "Rapid High Resolution Three Dimensional Reconstruction of Embryos with Episcopic Fluorescence Image Capture." 2004 Wiley-Liss, Inc. *Birth Defects Research* (Part C), vol. 72:213-223.

Winfried Denk and Heinz Horstmann. "Serial Block-Face Scanning Electron Microscopy to Reconstruct Three-Dimensional Tissue Nanostructure." Nov. 2004. PLoS Biology, vol. 2, No. 11, pp. 1900-1909.

Kuririan, AM and Leighton, SB. "Oxygen plasma etching of entire block faces improves the resolution and usefulness of serial scanning electron microscopic images." *Scan Electron Microsc.* 1983, Pt. 1877-85.

Leighton, SB. "SEM Images of block faces, cut by a miniature microtome within the SEM—a technical note." *Scan Electron Microsc.* 1981, Pt. 2:73-76. Abstract Only.

Kuririan, AM and Leighton, SB. "Oxygen plasma etching of entire block faces improves the resolution and usefulness of serial scanning electron microscopic images." *Scan Electron Microsc.* Pt. 1877-85. pp. 1877-1885 Attached.

Leighton, SB. "SEM Images of block faces, cut by a miniature microtome within the SEM—a technical note." *Scan Electron Microsc.* 1981, Pt. 2:73-76. pp. 73-76 Attached.

Microscience Group, Inc. "Our Technology." Abstract.

Microscience Group, Inc. "DVI Microimager™." (2 sheets), Abstract.

Tramu, G. et al. "An Efficient Method of Antibody Elution for the Successive or Simultaneous Localization of Two Antigens by Immunocytochemistry." *The Journal of Histochemistry and Cytochemistry* 1978. 26:4, pp. 322-324.

Blumer, Michael J.F. et al. "Ribbons on Semithin Sections: An Advanced Method with a new type of diamond knife." *Journal of Neroscience Methods* 2002. V. 120, pp. 11-16.

Ren, Ying et al. "Same Serial Section Correlative Light and Energy-filtered Transmission Electron Microscopy." *The Journal of Histochemistry and Cytochemistry* 2003. 51:5, pp. 605-612.

Wali, Naheed et al. "A Method for Collecting Semithin Epoxy Serial Section for Light Microscopy and 3-D Reconstruction." *Journal of Neroscience Methods* 1998. V. 23, pp. 91-94.

Merzel, J. "Preparation of Semithin Serial Sections of Epon Embedded Material." *Experieutia* 1971. V. 27, pp. 612-612.

Basgen, John M. et al. "Comparison of Methods for Counting Cells in the Mouse Glomerulus." *Experimental Nephrology* 2006. V. 103, pp. e-139-e148.

Warshawsky, H. et al. "A Three-dimensional Reconstruction of the Rods in Rat Maxillary Incisor Enamel." *The Anatomical Record* 1971. 169:3, pp. 585-591.

Coulter, H. David et al. "Video-Enhanced Technique for Detecting Neurophysin, Enkephalin, and Somatostatin Immunoreactivity in Ultrathin Sections of Cat Median Eminence." *The Journal of Histochemistry and Cytochemistry* 1986. 34:11, pp. 1405-1415.

Redecker, P. et al. "Syanptophysin—A Common Constituent of Presumptive Secretory Microvesicles in the Mammalian Pinealocyte: A Study of Rat and Gerbil Pineal Glands." *Journal of Neroscience Research* 1993. V. 34, pp. 79-96.

Redecker, Peter et al. "Munc-18-1 and Cystein string protein (CSP) in pinealocytes of the gerbil pineal gland." *Cell Tissue Res* 1998. V. 293, pp. 245-252.

Nanci, A. et al. "Routine Use of Backscattered Electron Imaging to Visualize Cytochemistry and Autoradiographic Reactions in Semithin Plastic Sections." *The Journal of Histochemistry and Cytochemistry* 1990. 38:3, pp. 403-414.

\* cited by examiner

OPTICAL IMAGING OF MOLECULAR CHARACTERISTICS OF BIOLOGICAL SPECIMEN

RELATED PATENT DOCUMENTS

This patent document claims the benefit, under 35 U.S.C. §119(e), of U.S. Provisional Patent Application No. 60/673,590, entitled "Fluorescence Microscopy" as was filed on Apr. 20, 2005.

FIELD OF THE INVENTION

The present invention relates generally to optical imaging, and more particularly to optically imaging a biological specimen.

BACKGROUND

Many imaging applications involve the use of optical systems such as microscopes and other lens arrangements to capture image information about inert and biological specimens. The captured images are used for a multitude of applications such as analysis of cell behavior, identification of tissue characteristics and more.

In many imaging applications, the internal structure of a specimen is desirably accessed and observed. For such applications, subsurface imaging techniques have been employed with some success. In some applications, portions of a specimen located at depths below a surface are imaged to facilitate three-dimensional imaging.

When imaging tissue, a variety of characteristics of the image and the imaging approach impact the value and usability of the imaging. For example, microscopic imaging applications often benefit from high resolution images. In addition, it is often desirable to identify and recognize a large number of different characteristics (e.g., different molecular components). However, obtaining images, and in particular high resolution images, has generally involved a tedious and time-consuming process, often requiring expensive analysis equipment. Many earlier approaches are also susceptible to significant noise in collected image data, tend to perturb the specimen undergoing analysis and are often quantitatively unreliable.

One field in which imaging has been useful is the field of biomedical analysis of disease and other conditions such as aging. Disease conditions and consequences of aging are related to molecular changes in cells that compose tissue. The analysis of cells has been challenging due to the extreme complexity of cells and tissues, the very large numbers of distinct cellular molecules that must be taken into account, and because molecules related to specific disease and aging mechanisms may exist in very low abundance and may thus be very hard to detect or measure.

These and other issues continue to present challenges to optical imaging and, in particular, to the optical imaging of the molecular characteristics of biological tissue.

SUMMARY OF THE INVENTION

The present invention is directed to overcoming the above-mentioned challenges and others related to applications discussed above and others. These and other aspects of the present invention are exemplified in a number of illustrated implementations and applications, some of which are shown in the figures and characterized in the claims section that follows.

Various aspects of the present invention are applicable to imaging tissue stained or otherwise marked using biologically-selective material. Some aspects are directed to iteratively staining and imaging a specimen such as a biological specimen in a manner that facilitates the rapid, accurate and detailed collection of image data from the specimen.

According to an example embodiment of the present invention, an approach to specimen analysis involves staining a surface, or block-face, of a specimen. The stained surface is imaged, after which a portion of the specimen is removed to expose a new surface. The exposed new surface is stained and evaluated. New surfaces are exposed, stained and evaluated using this approach, until a selected number of exposed surfaces have been evaluated. In certain applications, these approaches involve generating a three-dimensional image of the specimen by selectively combining images taken at different stained surfaces of the specimen. In other applications, different exposed surfaces are stained with different stains. In still other applications, multiple markers are applied with a particular stain to a surface, the markers selectively coupling to different molecules in the specimen, with the markers imaged and used to identify a molecular composition of the specimen. In various instances, the methods described here lend themselves to complete automation of every step.

According to another example embodiment of the present invention, an embedded biological specimen is analyzed with a repetitive approach. A surface portion of the embedded biological specimen is selectively stained, and the stained surface portion of the embedded biological specimen is evaluated. Relative to the surface portion, the embedded biological specimen is segregated (e.g., cut and removed) to expose another surface portion of the biological specimen. The above steps of staining and evaluating are repeated with each exposed surface portion. The evaluated stained surface portions are used to analyze the specimen along a depth of the specimen.

In a more particular example embodiment of the present invention, the molecular composition of a specimen is analyzed. The biological specimen is embedded in a resin to form a resin matrix with the biological specimen, the resin matrix having porosity characteristics that limit the penetration of stain. A stain is applied to a surface of the resin matrix, using the resin matrix to limit the depth of penetration of the stain below the surface. The stain selectively couples to molecules of the biological specimen near the surface. The stained surface of the resin matrix is imaged. After imaging, the stained portion of the resin matrix is separated, relative to the depth of penetration of the stain into the resin matrix, therein exposing an unstained surface of the resin matrix. A stain is then applied to the exposed surface of the resin matrix, again using the resin matrix to limit the depth of penetration of the stain below the exposed surface. The newly-applied stain selectively couples to molecules of the biological specimen near the exposed surface. The newly-stained exposed surface of the resin matrix is imaged. The staining, separating and newly-staining steps are repeated until a desirable number of images are obtained. In this regard, the images of a plurality of adjacent portions of the resin matrix are used to form a three-dimensional image of the specimen. The three-dimensional image is used to identify molecular characteristics of the specimen identified via the selective coupling of the stain.

The above overview is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of analyses, and has been found to be particularly useful for applications involving the optical imaging of biological specimens and related aspects thereof. While the present invention is not necessarily limited to such approaches, various aspects of the invention may be appreciated through a discussion of various examples using these and other contexts.

According to an example embodiment of the present invention, a specimen is imaged using an approach involving iteratively exposing a surface of the specimen, staining the exposed surface and imaging the exposed and stained surface. The surface of the specimen is iteratively exposed using an approach such as ultramicrotomy or other cutting approach, such as one of those discussed in connection with the Figures below. The stain facilitates imaging, and in some instances, includes one or more of a quantum-dot stain, an organic stain and/or a fluorescent-type stain such as a fluorescent dye and the Green fluorescent protein (GFP, a spontaneously fluorescent protein isolated from coelenterates such as the Pacific jellyfish, *Aequoria Victoria*) or other fluorescent proteins.

In the context of this discussion, the surface of a specimen generally includes a surface portion of the specimen to a depth into the specimen that can range from a few angstroms to several hundred nanometers, depending upon the application. In this regard, staining a surface of a biological specimen may involve staining a surface portion extending to a depth into the specimen (e.g., to about 50 nanometers into the specimen). Moreover, when the specimen is embedded in other materials such as resin, staining a surface of the specimen may involve staining a surface of the material in which the specimen is embedded (to a depth as discussed above).

The imaging involves a variety of approaches and/or combinations of approaches, depending upon the application. In some instances, the imaging involves the detection of light reflected from the stained surface of the specimen or from a portion of the specimen below the surface. In other instances, the imaging involves the detection of light fluoresced by the specimen. An optical detector is used to collect the light, with an image represented by the collected light being observed and/or converted to data that can be used to generate and/or store an image electronically.

Where light is generated on the specimen surface, e.g., via fluorescence, a variety of stimulation approaches are selectively implemented to simulate the specimen and encourage the fluorescence. In some applications, fluorescent material is embedded in the specimen. Light is directed to the specimen and stimulates the fluorescent material into emitting fluorescence, which is detected and used to image the specimen.

For a variety of applications, the specimen is embedded in a fixed arrangement, such as a fixed medium (e.g., resin) that holds the specimen generally stable for imaging. In some applications, the embedding involves a fixation step such as standard chemical fixation involving, for example, paraformaldehyde, glutaraldehyde, freezing (e.g., high-pressure or cryoprotection), freeze substitution and low-temperature embedding processes. Where the specimen is embedded in the fixed medium, some of the medium is removed when removing a portion of the specimen to expose a surface of the specimen.

In another example embodiment of the present invention, an automated fluidics system is adapted to move one or more staining liquids on and off a block face of a specimen to be imaged. A surface of the specimen is exposed, the fluidics system moves a staining liquid onto the exposed surface and the exposed surface is imaged. After imaging, a portion of the specimen is removed to expose a new surface (i.e., below a previously-exposed surface), the fluidics system moves a staining liquid onto the newly-exposed surface and the newly-exposed surface is imaged. The surface is iteratively exposed (e.g., using a microtome to remove a thin layer), stained with the fluidics system and imaged.

In some implementations, the fluidics system also washes the surface of the specimen. For example, after the exposed surface is stained, the fluidics system can supply a washing fluid to the specimen to remove excess staining solution before the surface is imaged.

In another example embodiment, a mechanical system moves a specimen being imaged between liquid locations, or compartments, to effect fluid exchanges. These fluid exchanges may involve, for example, staining and/or washing a surface of the specimen to be imaged. For instance, a specimen with an imaging surface exposed can be moved into contact with a staining compartment where stain is applied to the exposed surface. The mechanical system then moves the specimen into a position amenable to imaging and the specimen is imaged. After imaging, a new surface of the specimen is exposed, either at the imaging position or at a new position into which the mechanical system moves the specimen. After exposing of the new surface, the mechanical system moves the specimen into contact with the staining compartment, followed by movement into a position for imaging. In some applications, the mechanical system also moves the specimen into position for washing, between one or more of the above-discussed positions.

In some or all of the above embodiments involving a repeated or iterative exposure and imaging of new surfaces, multiple surface images are obtained and used to generate a three-dimensional image of the specimen.

In some or all of the above example embodiments, the staining approach involves mitigating depth related variations in staining efficiency that characterize imaging approaches where a single staining is carried out, followed by iterative imaging at different surface of the specimen. In connection with this approach, the staining is selectively implemented to limit the application of the stain to within a selective depth below an exposed surface of the specimen. For example, the depth of stain may selectively be controlled by one or more of: embedding the specimen in a fixed medium that limits stain penetration, applying relatively large staining particles, controlling the quantity of stain applied and/or controlling the time during which the stain remains in contact with the specimen. In some applications, an automatic stain-applying approach involves programming an arrangement to automatically apply stain in connection with these approaches, e.g., for selected times and/or with a metered (i.e., measured) amount of stain.

Certain applications also involve the use of a washing step to control the exposure of the specimen to stain. For instance, where a stain depth is desirably limited to a set depth (e.g., a selected number of microns, or less than one micron), stain is automatically applied to an exposed surface of a specimen, with a washing fluid subsequently automatically, applied to the exposed surface after a selected time period has passed.

Stains implemented with one or more approaches discussed herein include, for example, relatively large "quantum dot" conjugates, such as quantum dot labeled antibodies (e.g., quantum-dot fluorescent nanoparticle-conjugated primary antibodies), as staining reagents. The quantum dots are generally confined near the surface of the specimen, to depths of about 30-40 nanometers. In some applications, a specimen is embedded in a resin having porosity characteristics that limit the penetration of quantum dots (e.g., to a few nanometers into a resin matrix). The quantum dot staining components facilitate brightness, fade resistance and narrow emission spectra. The narrow emission spectra in turn facilitate the simultaneous multiplexing of many label species in one staining step. In this regard, some implementations of the staining approaches discussed herein selectively involve staining solutions including mixtures of many different antibodies (e.g., 10) applied in a single labeling step.

In certain embodiments, an indirect antibody immunostaining approach is implemented with secondary antibody reactions (used, e.g., for amplification). For instance, a first (often unlabeled, or otherwise difficult to detect) antibody is coupled to a particular target in a specimen. One or more second labeled antibodies (e.g., an antibody that fluoresces in a recognizable manner) are then attached to the primary antibody to facilitate detection.

In other embodiments, direct immunostaining approaches are implemented by attaching marker antibodies directly to a particular molecule. The marker antibodies are those that are readily detectable, such as those including quantum dot species coupled directly (or via an avidin-biotin coupling step) to a single antibody species. Once coupled to the particular molecule, the marker antibodies are detected and used to detect the presence of the particular molecule.

In some direct immunostaining approaches, two or more primary marker antibodies are used to selectively couple to different portions of a particular sample (e.g., to different molecules in the sample). The primary marker antibodies are separably detectable, and in some instances, fluoresce different colors that are detectable and distinguishable from one another. In this regard, a single analysis image can be used to identify two or more targets in a specimen, with information about the presence of the targets ascertained by associating the primary markers with particular targets to which they attach.

In some applications, the analysis of a sample is facilitated by one or more approaches to mitigating confusion often associated with imaging three-dimensional structures. In one application, the depth of quantum-dot material applied to a sample is limited to several (e.g., 30-40) nanometers below the surface of the sample, such that imaged targets near the surface are not obscured by similarly-marked targets at greater depths in the sample. In another application, a sample is iteratively sliced at thicknesses of between about 30-100 nanometers using an approach described herein, such that images of each slice are not obscured by stain in other portions of the sample. In still another application, a combination of controlling the depth of material staining of a sample and of a slicing approach are used to facilitate the imaging of the marker antibodies (and corresponding detection of targets to which the antibodies are attached).

In some implementations, iterative imaging as discussed above includes simultaneous imaging at a like number of emission spectral bands to image many (e.g., 10) different antigen distributions in connection with a single cycle of cutting, staining and imaging. The image is processed, either manually or automatically, to identify different markers via the spectral bands, thereby detecting antigen distributions relating to molecules (or other materials) with which the markers are associated.

In another example embodiment, a specimen is iteratively exposed, stained and imaged using different staining materials at subsequent iterations. In one example, different antigens are imaged in the volume of a single specimen using a repeating pattern of alternating stain mixtures applied to alternate cut surfaces. The depth of the stain application is selectively controlled to facilitate the subsequent staining of a lower surface (subsequently exposed) with a different stain, while inhibiting migration of a previously-used stain.

In another example embodiment of the present invention, a multitude of different antigens within a single specimen are imaged at an effective low sampling interval (e.g., one axial micrometer). Sections of the specimen are cut (to expose surfaces) at small intervals (e.g., less than about 250 nanometers and in some applications, less than about 50 nanometers), with each cut followed by a staining and imaging step. In one example application, 20 sections with a thickness of 50 nanometers are cut through 1 micrometer of a specimen. Each of the exposed surfaces is stained with a mixture of ten different antibodies, with 200 antigens detected simultaneously with a 1 micrometer axial resolution.

The staining is limited to a depth below a surface amenable to the selective application of stain to antigens within a thin surface corresponding to the cut interval. The staining is alternated through a sequence of different staining solutions with different quantum-dot-labeled antibodies each, and each surface is imaged at emission wavelength bands corresponding to the different wavelengths associated with each quantum-dot.

The specimen is imaged, using the different wavelengths to identify each appropriate quantum-dot and, accordingly, each antibody to which the quantum dot is coupled. In some applications, a wavelength multiplexing approach is implemented to facilitate such wavelength-based detection at a relatively rapid rate.

In some applications, one or more of the approaches herein are applied to the analysis of tissue biology areas in one or more of neuroscience, cancer biology and stem-cell biology. A marking (staining) material such as a quantum dot material is iteratively applied to the tissue undergoing analysis with cutting and imaging of the tissue between applications of the marking material. A series of images are collected and used to study the tissue, providing information about the tissue at relatively small increments of depth into the sample (e.g., 250 nanometers or less).

Many different types of specimen can be analyzed using the approaches described herein and shown in the figures. One example embodiment is directed to the analysis of synapse pairs in a specimen bearing a multitude of such pairs, with mitigation of vertical specimen confusion (i.e., that often results from the imaging of a relatively thick portion of a specimen bearing stained synapse pairs). The synapse pairs are stained with distinctly detectable markers for presynaptic and postsynaptic portions of the synaptic pairs (e.g., respectively using red and green colored markers).

A portion of the specimen containing the stained pairs is then imaged to obtain identifiable synapse pairs. In some applications, the stain is limited to a depth of less than about 50 nanometers to mitigate specimen confusion that can result when synapses at a greater depth are stained and accordingly appear in an image, resulting in a far greater number of synapses in a particular image and causing vertical specimen confusion.

In other applications, a thin (e.g., less than 50 nanometer) portion of the specimen is removed, then imaged, to mitigate the aforesaid vertical specimen confusion that characterizes thicker samples. In such applications, the staining may be limited to the thin portion of the specimen, such that a portion of the specimen exposed via the removal of the thin portion can then be stained and imaged independently from the removed portion of the specimen. With this approach, different stains can be used for synapses in a common specimen and at relatively small (e.g., less than 100 nanometer) vertical separation. Moreover, when automated as described in connection with FIGS. 1-3 below, this approach is implemented to achieve high-volume, rapid staining of specimen for a variety of analysis approaches.

In another example embodiment, each section cut from a specimen (for exposure of a new surface) for an iterative cutting and imaging approach is retained after it is removed from the specimen. Fluorescence volume imaging is performed by imaging the specimen and/or imaging the cut portion of the specimen removed therefrom. In some examples, microscale mass-spectroscopic analysis is carried out on a specific area of a specific section of a specimen in response to the detection of a specific feature by volume image analysis. In other examples, sections cut from the specimens are further analyzed using electron microscopy. In some applications, sections of the specimen are stored by placing them at addressable locations on the surface of a disk or other two-dimensional arraying surface.

For general information regarding imaging approaches and for specific information regarding imaging approaches that may be implemented in connection with one or more example embodiments of the present invention, reference may be made to U.S. Pat. No. 4,960,330 to Kerschmann, and to "Surface Imaging Microscopy, An Automated Method for Visualizing Whole embryo Samples in Three Dimensions at High Resolution, Ewald, McBride, Reddington, Fraser and Kerschmann, Dev Dyn. 2002 November; 225(3):369-75, both of which are fully incorporated herein by reference.

Figure 1:
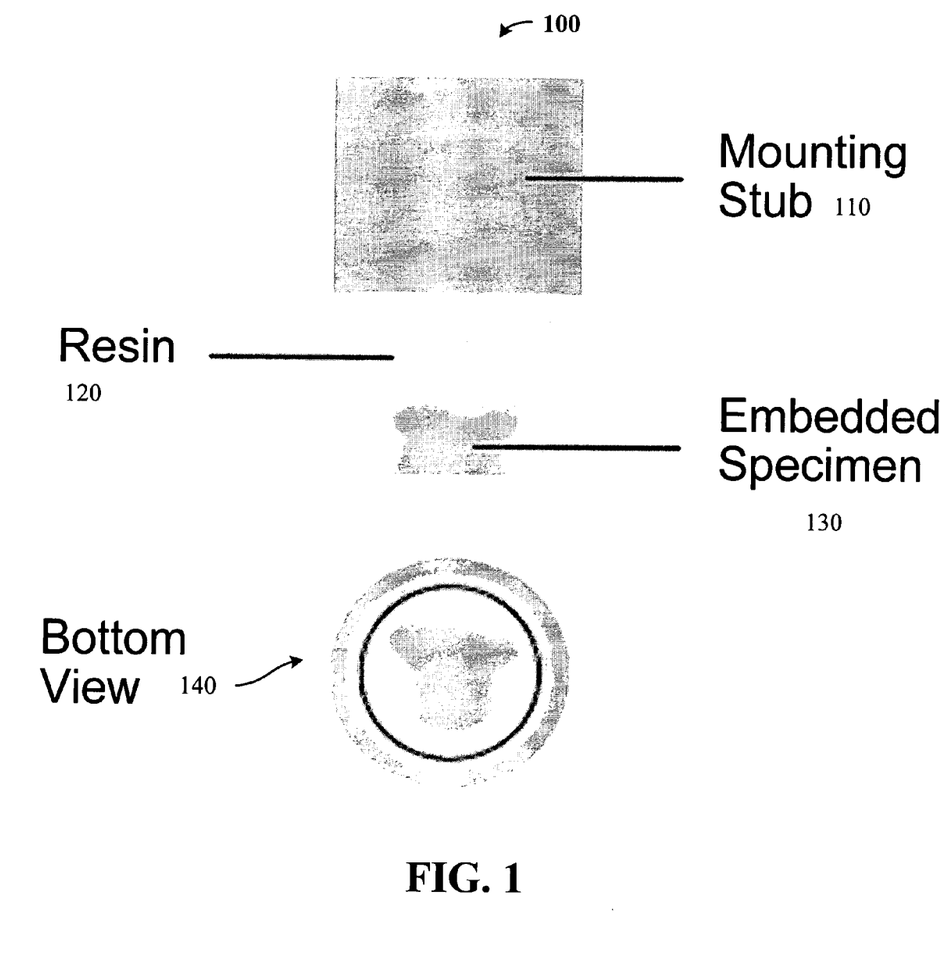
FIG. 1 shows a specimen carrier for presenting a specimen for iterative analysis, according to an example embodiment of the present invention.
Figure 2:
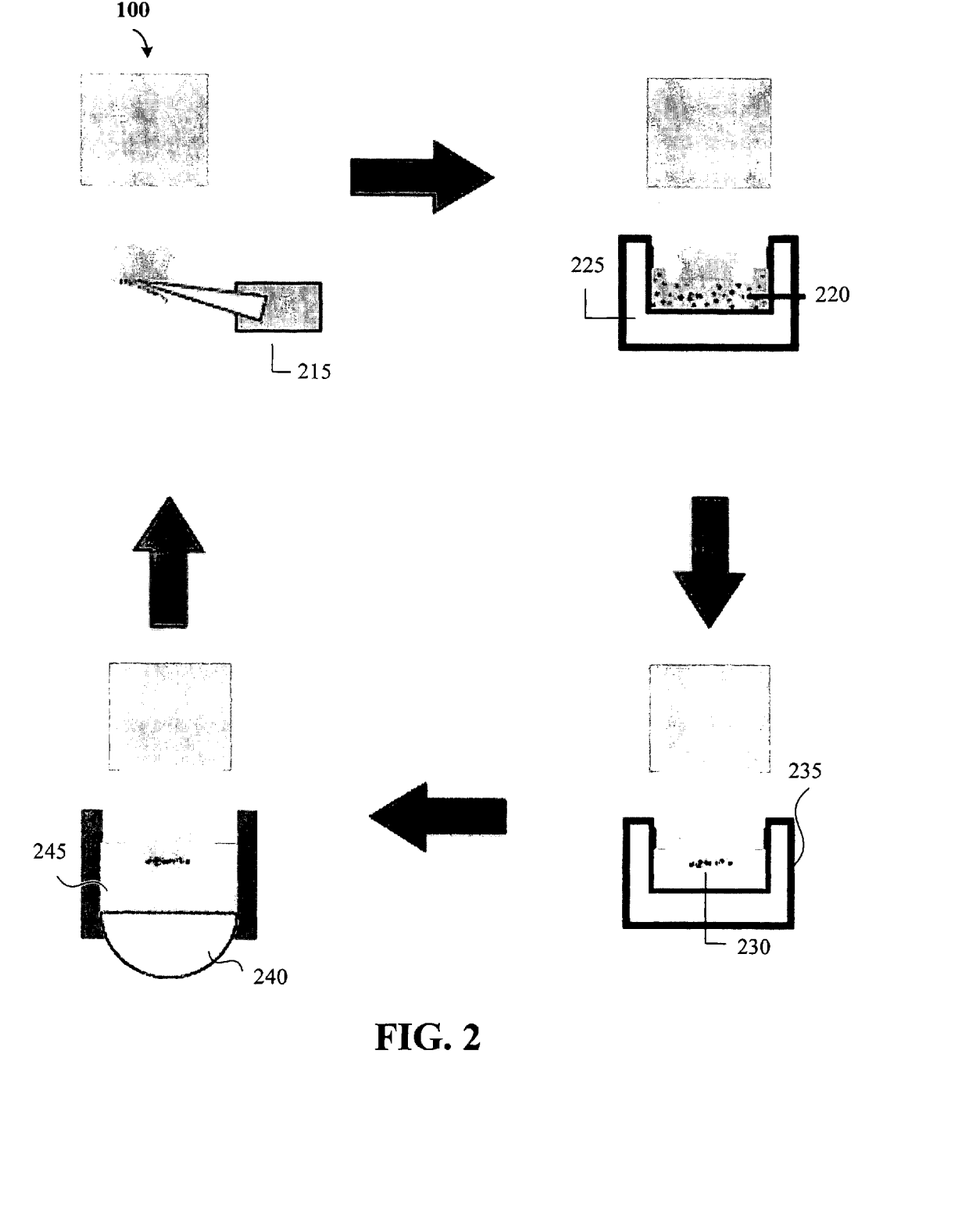
FIG. 2 shows an iterative imaging approach, according to another example embodiment of the present invention.
Figure 3A:
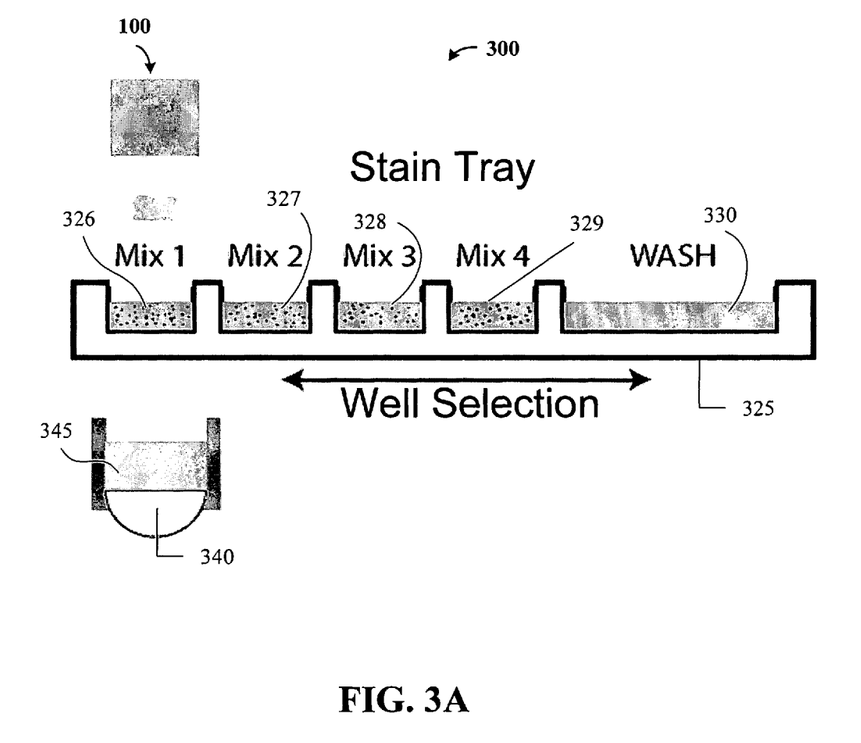
FIGS. 3A and 3B respectively show front and side views of an approach to automated specimen imaging, according to another example embodiment of the present invention.
Figure 3B:
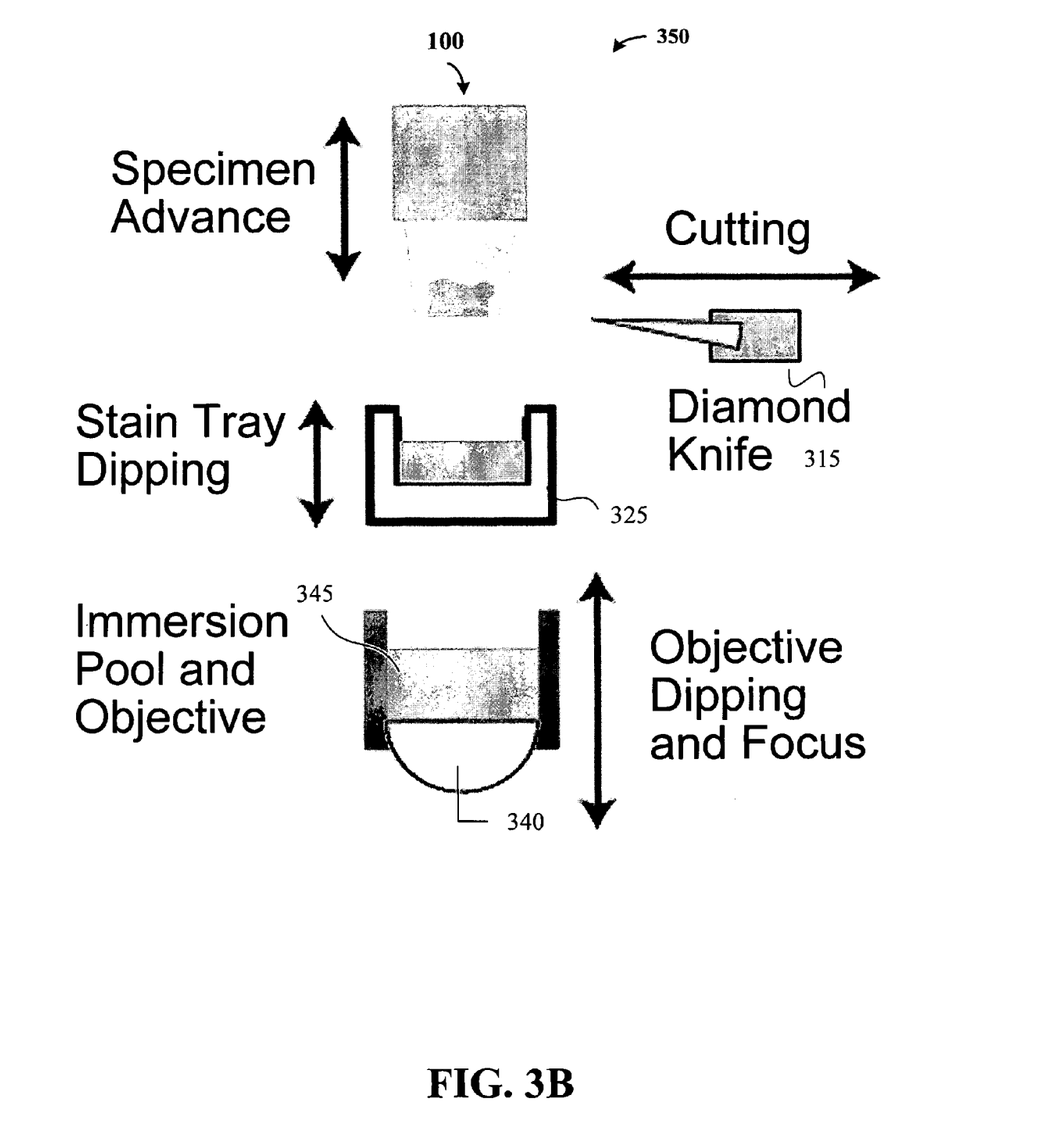

Turning now to the figures, FIG. 1 shows a specimen carrier 100 for iteratively imaging a specimen, according to another example embodiment of the present invention. The specimen carrier may, for example, be implemented in connection with an imaging approach as described above and/or as shown in and described in connection with the figures below (e.g., as shown in FIGS. 2-3B), as well as a variety of other iterative staining approaches.

The specimen carrier 100 includes a mounting stub 110 that couples to a resin block 120 having a specimen 130 embedded therein. The resin block 120 is selected from one or more of a variety of materials that are amenable to holding the specimen, such as a plastic resin matrix. The resin block 120 is bonded to the mounting stub 110 (e.g., a metallic material) for convenient mounting to an automated apparatus used for sectioning, staining and imaging the specimen. A bottom view 140 shows the specimen carrier 100 with embedded specimen 130.

The mounting stub 110 is depicted in FIG. 1 as a cylinder, the resin block 120 as a tapered cylinder and the specimen 130 itself as an irregular shape within the resin; however, a variety of shapes and arrangements are implemented with different example approaches, depending upon the application. Moreover, a variety of resin types can be implemented with this approach, some of which include acrylic resin, epoxy resin, LR white resin from London Resin Company of Berkshire, UK, and Lowicryl HM20 resin available from Polysciences, Inc. of Warrington, Pa.

As discussed above, the specimen carrier 100 is applicable for use in connection with a variety of embodiments and applications discussed herein. In this regard, FIGS. 2, 3A and 3B describe embodiments using a specimen carrier 100, similar to that shown above in FIG. 1, for illustration. However, these Figures are applicable for use with a variety of specimen carriers, similar to and/or different from (in arrangement and/or function) the specimen carrier 100.

FIG. 2 shows a cyclic imaging approach, according to another example embodiment of the present invention. At step 1, a knife 215 is used to cut a portion of a specimen embedded in a specimen carrier 100 as shown in FIG. 1. Where a specimen is first introduced with an exposed portion thereof (e.g., without resin covering the specimen), the first cutting step is omitted and the specimen carrier 100 directly undergoes a staining step a step 2 discussed below.

At step 2, the specimen carrier 100, having an exposed portion of the specimen 130, is introduced to a stain 220 in a staining container 225. The stain includes a mix "n," where "n" represents one or more of a variety of stain materials, such as fluorescent stain materials, a mixture of several different quantum dots species each conjugated to a different species of antibody, or others discussed herein.

At step 3, the specimen is washed using a wash material 230 in a wash container 235. The wash material 230 is selected for washing the specimen, e.g., to remove excess stain and leave behind staining moieties, such as antibodies and conjugated antibodies that have reacted specifically with an embedded biological specimen.

In some applications, the staining container 225 and the wash container 235 are the same container, with stain 220 and wash material 230 iteratively introduced to the container. In other applications, the staining container 225 and the wash container 235 are implemented separately, with the specimen carrier 100 being moved between the containers. The wash step at step 3 is also selectively carried out between steps 1 and 2, or moved after the imaging step 4, discussed next.

At step 4, the specimen is imaged using an imaging apparatus 240 such as a microscope or camera. In one example, the specimen is imaged via spectral fluorescence imaging to detect and discriminate numerous species of quantum dots. In some applications, an immersion fluid 245 such as water is used to facilitate resolution, light collection efficiency or other purposes. As with the previous steps, the specimen carrier 100 is moved into position to facilitate the imaging.

After imaging, the specimen undergoes another cycle beginning again at step 1. A number of iterative cycles are carried out, with the total number varying to suit particular applications. In some instances, as discussed above, a specimen is iteratively cut, stained and imaged at relatively small depth increments for subsequent cuts, facilitating the generation of iterative images that, when combined, show a three-dimensional image of the specimen.

The specimen carrier 100 is positioned using one or more of a variety of approaches. In one implementation, the cyclic imaging approach shown in FIG. 2 is effected with a stationary specimen carrier 100, with the respective steps being carried out using an electromechanical arrangement that moves cutting, staining, washing and imaging arrangements into position with the specimen carrier 100, for respective steps 1, 2, 3 and 4.

In another implementation, an electromechanical actuator such as a robotic arm and/or a multi-axis positioning arrangement are used to manipulate the specimen carrier 100. The mounting stub 110 is affixed to the electromechanical actuator, which positions the specimen carrier 100 for cutting, staining and/or other processing.

In another application involving the arrangement and approach shown in FIG. 2, the specimen carrier 100 is moved to position the specimen, with at least one of the cutting, staining, washing and imaging arrangements also moving to facilitate analysis thereof. For instance, where a spatial arrangement between the specimen carrier 100 and the knife 215 is used to expose a surface of a specimen, both the specimen carrier and the knife can be used to achieve the spatial arrangement. In some applications, two such components are simultaneously moved to achieve a particular relative motion. In other applications, each of two such components are iteratively moved to position the specimen (e.g., with the specimen carrier 100 moving vertically to position the specimen for cutting of a thin slice thereof, and the knife 215 moving laterally to cut the positioned specimen).

FIG. 3A shows a front view 300 and FIG. 3B a side view 350 of an approach to automated specimen imaging, according to another example embodiment of the present invention. This approach shown in FIGS. 3A-3B may implement a variety of approaches for positioning a specimen for analysis, and for illustrative purposes, is shown implementing the specimen carrier 100 of FIG. 1. In some applications, the automation in FIGS. 3A-3B is implemented with the approach shown in FIG. 2.

The side view 350 in FIG. 3B shows the specimen carrier 100, a diamond knife 315 for exposing a surface of the specimen, a dipping tray 325 that holds stain for staining the specimen and wash material for washing the specimen, and an imaging apparatus 340 having an immersion pool 345 and an imaging device such as an objective lens.

The front view 300 in FIG. 3A shows the specimen carrier 100 with the dipping tray 325, which has four mix containers 326, 327, 328 and 329, as well as a wash container 330, and the imaging apparatus 340. Each of the mix containers 326-329 are selectively implemented to hold similar or different types of stain. As described above, different stains may be used during subsequent imaging cycles, and in this regard, the dipping tray 325 facilitates the introduction of the different stains via the use of different ones of the mix containers 326-329.

The specimen carrier 100, diamond knife 315, stain dipping tray 325 and the imaging apparatus 340 are all selectively positioned to achieve a staining cycle. In one application, the specimen carrier 100 is advanced for cutting purposes, with the other items (diamond knife 315, dipping tray 325 and imaging apparatus 340) moved into position with the specimen carrier.

When the specimen is to be cut, the specimen carrier 100 moves the specimen in a small increment (e.g., 100 nanometers), relative to an initial or previous cut position, with the diamond knife 315 being actuated horizontally once the specimen is in position and while the specimen carrier 100 is held stationary. After a portion of the specimen has been cut to expose a surface, the dipping tray 325 is moved horizontally into position to align one of the mix containers 326-329 or the wash container 330 with the specimen carrier, and subsequently moved vertically into position to contact material in the dipping tray with the specimen.

After the specimen has been stained (and, where appropriate, washed) with the dipping tray 325, the dipping tray is actuated vertically away from the specimen carrier 100 and horizontally to facilitate a path between the specimen carrier and the imaging apparatus 340. With the dipping tray 325 out of the way, the imaging apparatus 340 is moved vertically into position with the specimen carrier 100 for imaging the specimen. Where the immersion pool 345 is used, the imaging apparatus 340 is moved vertically such that the specimen is immersed in the immersion pool, and an image of the specimen is taken.

In connection with another example embodiment of the present invention, an antigen recovery approach is implemented in connection with the approach shown in FIG. 3A and FIG. 3B. The specimen is treated with heat and with reagents and buffers (e.g., using an aqueous buffer in the dipping tray 325) to facilitate the detection of antigens or features of the specimen. The antigen recovery step is selectively performed prior to staining. For general information regarding biological analysis and for specific information regarding approaches to antigen recovery that may be used in connection with one or more example embodiments, reference may be made to U.S. Pat. No. 6,855,292 to Angros, which is fully incorporated herein by reference.

Figure 4:
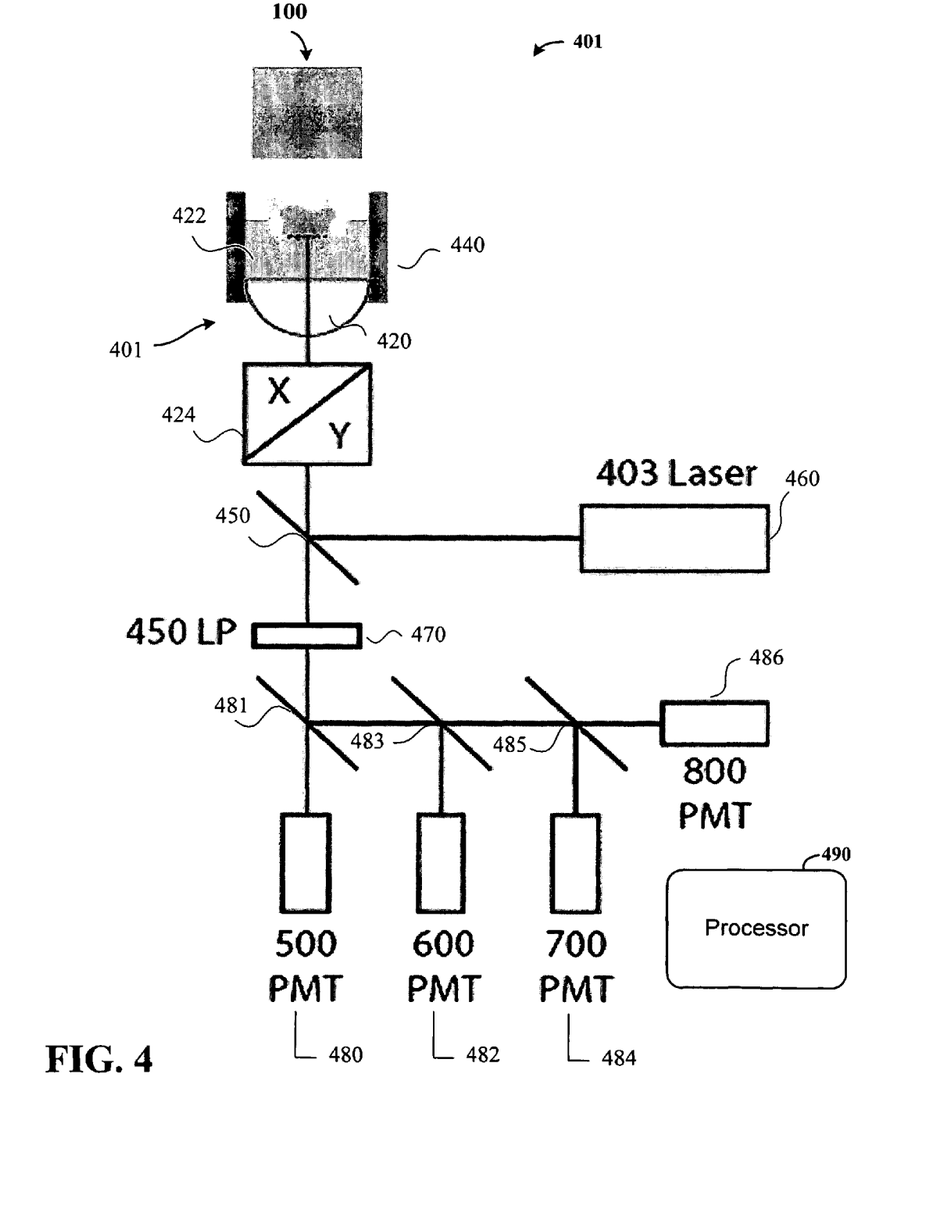
FIG. 4 shows a laser scanning arrangement that is selectively used in connection with specimen imaging approaches, such as those shown in FIGS. 1-3, according to other example embodiment of the present invention.
Figure 5:
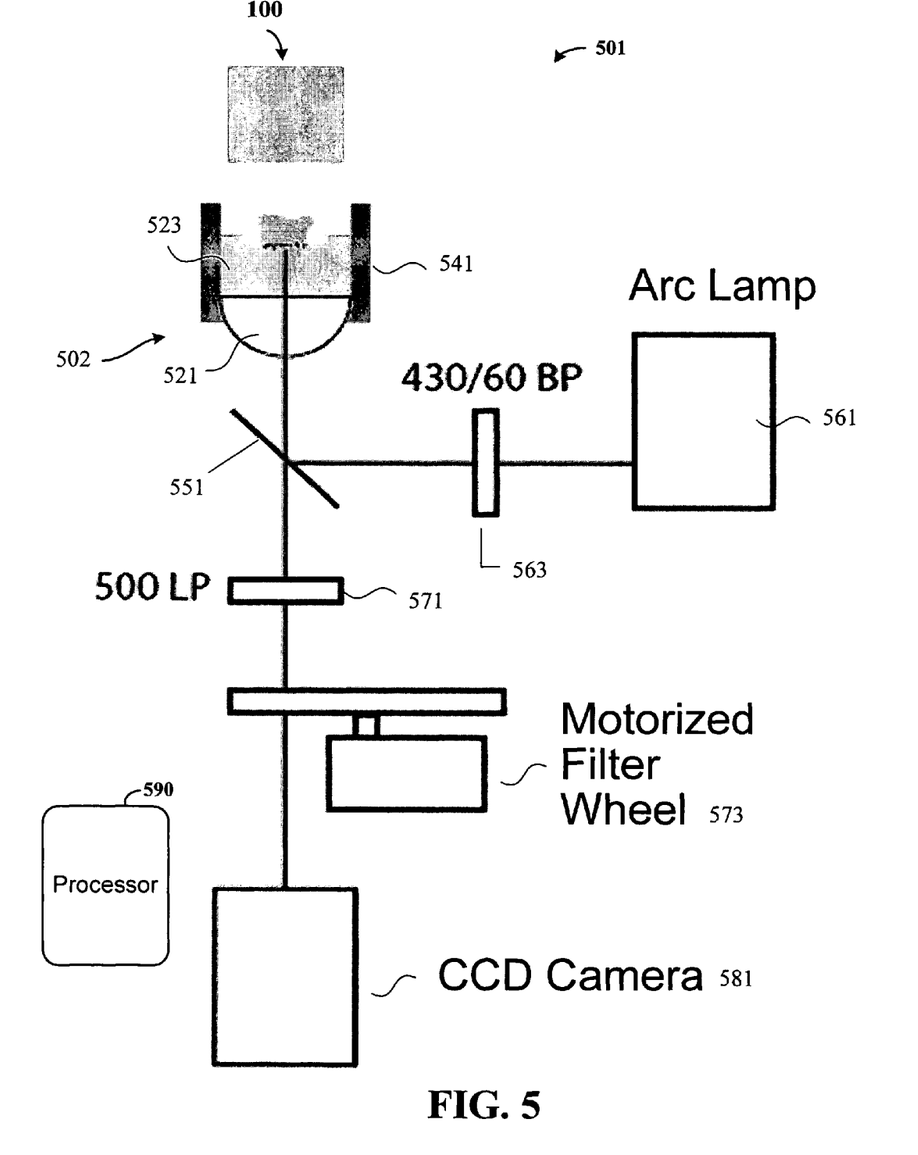
FIG. 5 shows a charge-coupled device (CCD) widefield system that is selectively used in connection with specimen imaging approaches, such as those shown in FIGS. 1-3, according to another example embodiment of the present invention.

FIG. 4 and FIG. 5 show example imaging arrangements that are selectively used in connection with specimen imaging approaches, including those discussed herein, according to other example embodiments of the present invention. The arrangements shown in FIG. 4 and FIG. 5 are implemented, for example, with the approaches discussed above in connection with FIGS. 1-3B.

The specimen carrier 100 discussed above is selectively used with the arrangements shown in FIG. 4 and FIG. 5, and in this regard, the examples shown implement the specimen carrier. In certain applications involving fluorescent dot stains, the arrangements shown in FIG. 4 and FIG. 5 are configured for discriminating multiple fluorescence emission wavelengths and implemented, for example, in connection with wavelength-based approaches including those discussed above.

Beginning with FIG. 4, a laser scanning arrangement 401 includes an imaging arrangement 440 having an objective lens 420 and an immersion pool 422. A laser 460 directs light through a beam splitter 450 and a scanning arrangement 424, such as a two-axis galvo scanner, to the imaging arrangement 440 and the specimen at the specimen carrier 100. Response light from the specimen is passed back through the scanning arrangement 424 and the beam splitter 450 to a dichroic 470 (shown passing wavelengths above 450 nanometers) and to a bank of photomultiplier (PMT) detectors 480, 482, 484 and 486. Beam splitters 481, 483 and 485 respectively split the response light to direct it to all of the PMT detectors, at different optical wavelength bands, to facilitate the discrimination of different quantum dot colors. By way of example, the respective PMTs 480, 482, 484 and 486 detect broad bands of optical spectrum respectively at 500, 600, 700 and 800 nanometer wavelengths. A processor 490, such as a computer and/or other imaging processing circuits and arrangements used with PMTs, uses information (i.e., a signal) from the PMTs to form an image of the specimen and, where appropriate, a three-dimensional image.

FIG. 5 shows a charge-coupled device (CCD) widefield system 502, according to another example embodiment of the present invention. Light is generated in the CCD widefield system 502 by an arc lamp light source 561, which passes light through a bandpass filter 563 (shown passing light of wavelengths between 530 and 60 nanometers) and a beam splitter 551 to an imaging arrangement 541. The imaging arrangement includes an objective lens 521 and an immersion pool 523, and passes light from the arc lamp 561 to a specimen at the specimen carrier 100.

Response light from the specimen passes through the beam splitter 551, through a dichroic 571 (shown passing wavelengths above 500 nanometers) and a motorized emissions filter wheel 573 before reaching a CCD camera 581. The motorized emissions filter wheel 573 has multiple wavelength-selective filters in different filter wheel positions that facilitate the discrimination of different quantum dot colors by sequentially imaging across different wavelength bands. A processor 590, such as a computer and/or other imaging processing circuits and arrangements used with CCD cameras, uses information (i.e., a signal) from the CCD camera 581 to form an image of the specimen and, where appropriate, a three-dimensional image.

Figure 6:
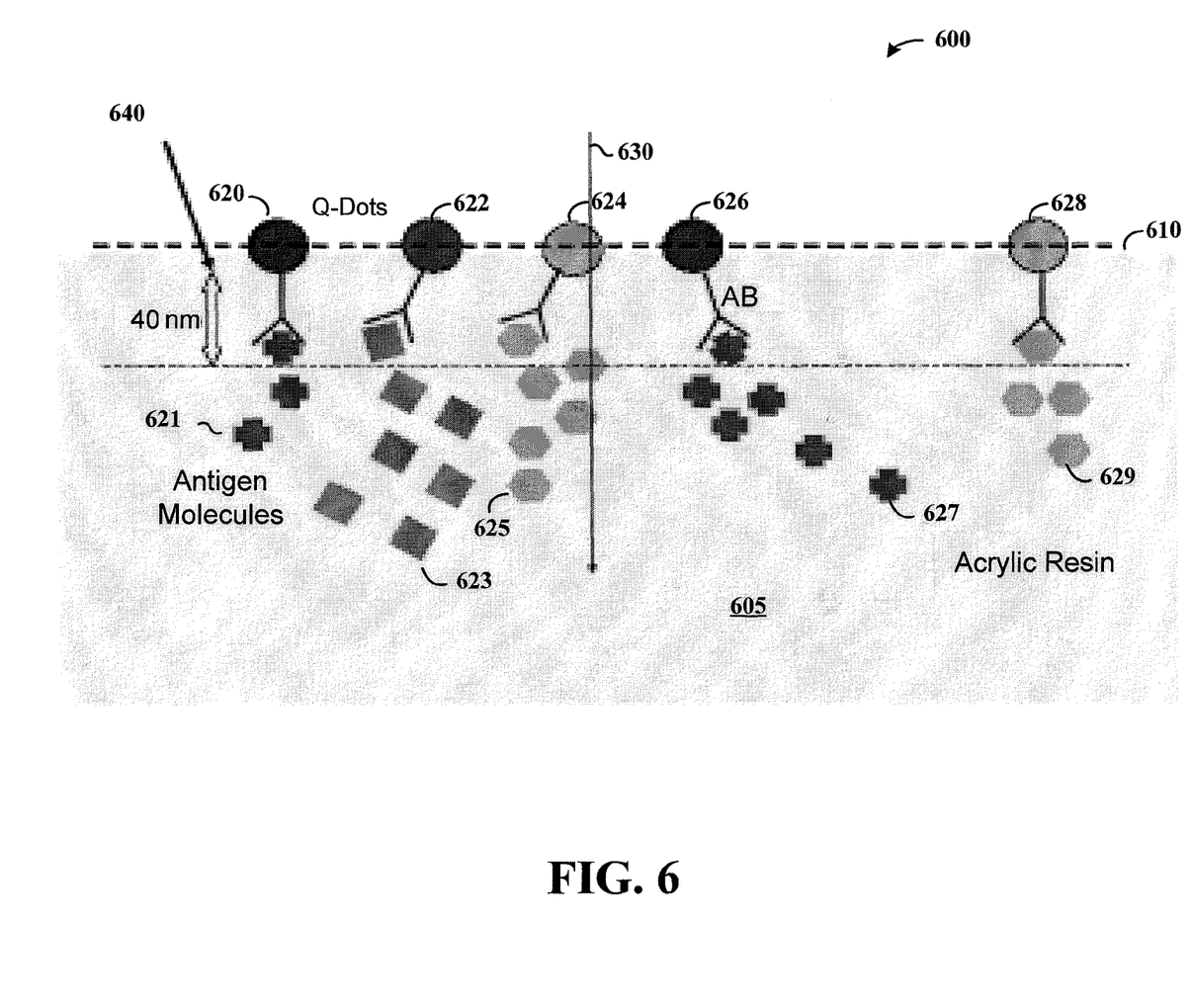
FIG. 6 shows a specimen arrangement implemented for iterative analysis via quantum-dot marking with a wavelength-multiplexing type approach, according to another example embodiment of the present invention.

FIG. 6 shows a quantum-dot based arrangement 600 implemented for imaging target species, according to another example embodiment of the present invention. A specimen of interest including antigen molecules (groups 621, 623, 625, 627 and 629 of different molecule types are shown) is embedded with low extraction in an acrylic resin matrix 605. An aqueous suspension of quantum-dot-conjugated antibodies (620, 622, 624, 626 and 628 shown, each represented with a circular quantum dot and Y-shaped antibody) are applied to an upper surface 610 of the resin 605, allowing the antibodies to bind to cognate specific antigens within 30-40 nanometers of the surface as shown by double arrow 640. Here, each of the respective antibodies 620, 622, 624, 626 and 628 are shown coupled to a single antigen in each group of antigens by way of example.

In some applications, the upper surface 610 is cut using, for example, an approach such as that shown in FIGS. 1-3 and described above, with antibodies reapplied iteratively as appropriate with newly-exposed surfaces as portions of the acrylic resin matrix are removed. The surface is washed after application of the antibodies, and imaged (e.g., along an optical axis 630). The resulting collected images facilitate the characterization of a planar distribution of fluorescent quantum dots that reveal (e.g., encode) the distribution of antibodies (and coupled antigen molecules) in a superficial plane of the specimen. By iteratively staining and imaging in this manner, the planar fluorescence distribution of the arrangement 600 can be imaged in ways that provide sensitivity and resolution along three volume axes.

Referring again to FIG. 6, the resin matrix 605 is selected to inhibit the penetration of quantum-dots beyond a selected depth. The resin material 605 has porosity characteristics that prevent the penetration of the quantum-dot-conjugated antibodies deep below the upper surface 610. In some applications, the quantum dots are limited in penetration depth to within a few nanometers of the upper surface 610, with the antibodies conjugated thereto extending a bit deeper below the upper surface and coupling to antigens therein.

In another example embodiment of the present invention, a fluorescent microscope arrangement and approach involves imaging a specimen in a manner not inconsistent with one or more of the applications described herein and/or shown in the figures. The detectable planar distribution of fluorescence, facilitated by iterative exposing and staining of a surface, facilitates desirable spatial resolution (e.g., increases spatial resolution). The following references numbered 1-8 describe approaches to high-resolution fluorescence imaging and which describe applications to which one or more of the example embodiments discussed herein can be applied; each of these references are fully incorporated by reference:

1. Heintzmann R, Jovin T M, Cremer C. Saturated patterned excitation microscopy-a concept for optical resolution improvement. J Opt Soc Am A Opt Image Sci Vis. 2002 August; 19(8):1599-609.
2. Hell S W, Dyba M, Jakobs S. Concepts for nanoscale resolution in fluorescence microscopy. Curr Opin Neurobiol. 2004 October; 14(5):599-609.
3. Hell S W. Toward fluorescence nanoscopy. Nat Biotechnol. 2003 November; 21(11):1347-55. Review. PMID: 14595362 [PubMed—indexed for MEDLINE]
4. Hell S W, Schrader M, van der Voort H T. Far-field fluorescence microscopy with three-dimensional resolution in the 100-nm range. J Microsc. 1997 July; 187 (Pt 1):1-7.
5. Klar T A, Jakobs S, Dyba M, Egner A, Hell S W. Fluorescence microscopy with diffraction resolution barrier broken by stimulated emission. Proc Natl Acad Sci USA. 2000 Jul. 18; 97(15):8206-10.
6. Gustafsson M G. Nonlinear structured-illumination microscopy: wide-field fluorescence imaging with theoretically unlimited resolution. Proc Natl Acad Sci USA. 2005 Sep. 13; 102(37):13081-6.
7. Gustafsson M G. Surpassing the lateral resolution limit by a factor of two using structured illumination microscopy. J. Microsc. 2000 May; 198 (Pt 2):82-7.
8. Gustafsson M G. Extended resolution fluorescence microscopy. Curr Opin Struct Biol. 1999 October; 9(5):627-34. Review.

In some applications, one or more of the approaches described in the above references are implemented for obtaining images in connection with an example embodiment described herein. For instance, referring to the arrangements and approaches described in connection with FIG. 3A and FIG. 3B, an illumination approach described in one or more of the above references can be used in connection with imaging via the objective 340 (or in place thereof).

In certain applications, digital image processing approaches as described in the above references are selectively implemented for processing specimen images obtained in accordance with one or more example embodiments described herein. For instance, the linear and non-linear structured illumination approaches as described in the Heintzmann, et al. and Gustafsson references (numbers 1 and 6-8 above) are selectively implemented with a CCD type approach, such as that shown in and described in connection with FIG. 5. In addition, the STED approaches as described in the works by Hell and colleagues (numbers 2-5 above) are selectively applied with laser scanning approaches, such as that shown in and described in connection with FIG. 4.

While certain aspects of the present invention have been described with reference to several particular example embodiments, those skilled in the art will recognize that many changes may be made thereto without departing from the spirit and scope of the present invention, aspects of which are set forth in the following claims.

What is claimed is:

1. A method for analyzing an embedded biological specimen, the method comprising:
    selectively staining a surface portion of the embedded biological specimen;
    evaluating the stained surface portion of the embedded biological specimen;
    relative to the surface portion, segregating the embedded biological specimen to expose another surface portion of the biological specimen;
    repeating the above steps of staining and evaluating with each exposed surface portion and, therefrom, using the evaluated stained surface portions to analyze the specimen along a depth of the specimen.

2. The method of claim 1, wherein selectively staining a surface portion of the embedded biological specimen includes staining the biological specimen to a depth of less than about 100 nanometers into the embedded specimen.

3. The method of claim 1, wherein selectively staining a surface portion of the embedded biological specimen includes staining the biological specimen with a quantum-dot stain to a depth of less than about 50 nanometers into the embedded specimen.

4. The method of claim 1, further including, prior to staining the biological specimen, embedding the biological specimen in a medium.

5. The method of claim 4, wherein embedding the biological specimen in a medium includes embedding the biological specimen in a resin-type matrix that limits the depth of penetration of stain into the embedded biological specimen.

6. The method of claim 1, wherein segregating the embedded biological specimen includes removing substantially all of the selectively stained surface portion.

7. The method of claim 1, wherein selectively staining a surface portion of the embedded biological specimen includes directly immunostaining the biological specimen.

8. The method of claim 1, wherein selectively staining a surface portion of the embedded biological specimen includes indirectly immunostaining the biological specimen.

9. The method of claim 1, wherein repeating the above step of staining includes staining different surface portions of the embedded biological specimen with different stains.

10. The method of claim 1, wherein selectively staining a surface portion of the embedded biological specimen includes staining the biological specimen with a plurality of different antibodies.

11. The method of claim 1, wherein evaluating the stained surface portion includes imaging the stained surface portion, and wherein using the evaluated stained surface portions to analyze the specimen along a depth of the specimen includes forming a three-dimensional image of the specimen from the stained surface portions.

12. The method of claim 11, wherein using the evaluated stained surface portions to analyze the specimen along a depth of the specimen includes using wavelength multiplexing to identify a plurality of different stains in the specimen.

13. The method of claim 1, further including
    labeling the biological specimen with green fluorescent protein (GFP) prior to embedding the biological specimen,
    embedding the GFP-labeled biological specimen in an acrylic resin, and
    wherein evaluating the stained surface portion of the embedded biological specimen includes evaluating residual fluorescence of the GFP.

14. The method of claim 1, further including subjecting the embedded biological specimen to an antigen recovery treatment to chemically modify a surface portion of the embedded biological specimen to expose an antigen therein.

15. A method for analyzing the molecular composition of a specimen, the method comprising:
    embedding a biological specimen in a resin to form a resin matrix with the biological specimen, the resin matrix having porosity characteristics that limit the penetration of stain;
    applying a stain to a surface of the resin matrix, using the resin matrix to limit the depth of penetration of the stain into the resin matrix, the stain selectively coupling to molecules of the biological specimen at a surface portion of the resin matrix;
    imaging the stained surface portion of the resin matrix;
    separating the stained surface portion of the resin matrix at a location determined from the depth of penetration of the stain into the resin matrix, therein exposing a new surface of the resin matrix;
    repeating the steps of applying a stain, imaging and separating for each exposed new surface of the resin matrix;
    using the images of a plurality of stained surface portions of the resin matrix to form a three-dimensional image of the specimen; and
    using the three-dimensional image to identify molecular characteristics of the specimen identified via the selective coupling of the stain.

16. The method of claim 15, wherein applying a stain to a surface of the resin matrix includes applying a quantum-dot-conjugated antigen stain and using the quantum dots and the porosity of the resin matrix to limit the depth of penetration of the stain into the resin matrix.

17. The method of claim 15, wherein applying a stain to a surface of the resin matrix includes selectively coupling stain to a particular type of molecule of the biological specimen to mark the particular type of molecule for imaging thereof.

18. A system for analyzing an embedded biological specimen, the system comprising:
    a staining arrangement configured for selectively staining a surface portion of the embedded biological specimen;
    an evaluating arrangement configured for evaluating the stained surface portion of the embedded biological specimen;
    a segregating arrangement configured for segregating the embedded biological specimen, relative to the surface portion, to expose another surface portion of the biological specimen;
    wherein the staining and evaluating arrangements repeat the steps of staining and evaluating with each exposed surface portion of the biological specimen for use in evaluating the specimen along a depth of the specimen.

19. The system of claim 18, wherein the staining arrangement is configured and arranged to stain the embedded biological specimen with different stains during subsequent cycles of staining, imaging and segregating, whereby adjacent portions of the biological specimen are stained with different stains.

20. The system of claim 18, wherein the segregating arrangement is adapted to separate a layer of the specimen having a thickness of less than about 50 nanometers to facilitate the separate staining and imaging of embedded molecules in the specimen having a spatial separation of less than about 100 nanometers.

21. The system of claim 18, wherein the evaluating arrangement includes an imaging arrangement adapted to image each stained surface portion of the embedded biological specimen.

22. The system of claim 21, wherein the evaluating arrangement includes a circuit arrangement adapted to combine images of the stained surface portions into a three-dimensional image for evaluating the specimen.

23. A method for analyzing an embedded biological specimen, the method comprising:
   selectively staining a surface portion of the embedded biological specimen;
   evaluating the stained surface portion of the embedded biological specimen;
   relative to a depth of stain of the surface portion, segregating the embedded biological specimen to expose another surface portion of the biological specimen;
   repeating the above steps of staining, evaluating each exposed surface portion, and segregating the embedded biological specimen, and using the evaluated stained surface portions to analyze the specimen along a depth of the specimen.

24. The method of claim 23, further including, prior to staining the biological specimen, embedding the biological specimen in a medium and wherein embedding the biological specimen in a medium includes embedding the biological specimen in a resin-type matrix that limits the depth of penetration of stain into the embedded biological specimen.

25. The method of claim 23, wherein evaluating the stained surface portion includes imaging the stained surface portion, and wherein using the evaluated stained surface portions to analyze the specimen along a depth of the specimen includes forming a three-dimensional image of the specimen from the stained surface portions.

26. The method of claim 23, wherein repeating the above step of staining includes staining different surface portions of the embedded biological specimen with different stains.

* * * * *